(12) United States Patent
Slenker et al.

(10) Patent No.: US 8,790,301 B2
(45) Date of Patent: Jul. 29, 2014

(54) SYSTEMS AND METHODS FOR BIOFILM REMOVAL, INCLUDING A BIOFILM REMOVAL ENDOSCOPE FOR USE THEREWITH

(75) Inventors: Dale E. Slenker, Jacksonville, FL (US); Cecil O. Lewis, Jacksonville, FL (US); Gerould W. Norman, Jacksonville, FL (US); John R. Prisco, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/495,564

(22) Filed: Jun. 13, 2012

(65) Prior Publication Data

US 2012/0253125 A1    Oct. 4, 2012

Related U.S. Application Data

(63) Continuation of application No. 11/680,781, filed on Mar. 1, 2007, now Pat. No. 8,206,349.

(51) Int. Cl.
| | |
|---|---|
| *A61B 1/12* | (2006.01) |
| *A61B 1/005* | (2006.01) |
| *A61B 17/3203* | (2006.01) |
| *A61B 1/00* | (2006.01) |
| *A61B 1/012* | (2006.01) |
| *A61M 1/00* | (2006.01) |
| *A61B 1/015* | (2006.01) |

(52) U.S. Cl.
CPC ......... *A61B 17/3203* (2013.01); *A61B 1/00091* (2013.01); *A61B 1/0125* (2013.01); *A61M 1/0039* (2013.01); *A61B 1/015* (2013.01); *A61B 1/12* (2013.01)
USPC ............... 604/109; 604/19; 604/28; 604/275; 604/516; 606/101

(58) Field of Classification Search
CPC ........... A61B 17/3203; A61B 1/00091; A61B 1/0125; A61B 1/015; A61B 1/12; A61M 1/0039
USPC ........... 604/19, 21–22, 27–28, 35, 39, 43–44, 604/48, 500, 514, 516, 164.01, 164.12; 606/101, 129, 139, 153
See application file for complete search history.

(56) References Cited

U.S. PATENT DOCUMENTS

| | | |
|---|---|---|
| 1,487,252 A | 3/1924 | Lore |
| 1,843,169 A | 2/1932 | McKesson |

(Continued)

FOREIGN PATENT DOCUMENTS

| | | |
|---|---|---|
| EP | 0184778 A2 | 6/1986 |
| FR | 2109115 A5 | 5/1972 |

(Continued)

OTHER PUBLICATIONS

Y. Zhang et al., "Detection of *Streptococcus pneumoniae* in Whole Blood by PCR," Journal of Clinical Microbiology, Mar. 1995, pp. 596-601.

(Continued)

*Primary Examiner* — Quynh-Nhu H Vu
(74) *Attorney, Agent, or Firm* — Dicke, Billig & Czaja, PLLC (57) ABSTRACT

Systems and methods of removing bacterial biofilm from a target site using a biofilm removal endoscope. The endoscope has an insertion portion including an imaging channel terminating at a viewing window and an irrigation channel terminating at a nozzle. The imaging and irrigation channels are permanently affixed relative to one another. The insertion portion is inserted into the patient, with a working end thereof being disposed proximate the target site. The target site is imaged and a flow of fluid is dispensed via the nozzle to mechanically remove bacterial biofilm from the target site.

9 Claims, 6 Drawing Sheets

(56) References Cited

U.S. PATENT DOCUMENTS

| | | | |
|---|---|---|---|
| 1,987,907 A | | 1/1935 | Jenkins |
| 2,243,299 A | | 5/1941 | Travers |
| 2,280,992 A | | 4/1942 | Wright et al. |
| 2,812,765 A | | 11/1957 | Tofflemire |
| 3,208,145 A | | 9/1965 | Turner |
| 3,452,745 A | | 7/1969 | Hutchinson et al. |
| 3,470,876 A | | 10/1969 | Barchilon |
| 3,749,090 A | | 7/1973 | Stewart |
| 3,980,078 A | | 9/1976 | Tominaga |
| 4,238,072 A | * | 12/1980 | Licursi ............................ 239/1 |
| 4,282,867 A | | 8/1981 | Du Toit |
| 4,299,221 A | | 11/1981 | Phillips et al. |
| 4,397,640 A | | 8/1983 | Haug et al. |
| 4,408,598 A | | 10/1983 | Ueda |
| 4,436,087 A | * | 3/1984 | Ouchi ........................... 600/106 |
| 4,487,600 A | | 12/1984 | Brownlie et al. |
| 4,517,962 A | | 5/1985 | Heckele |
| 4,519,385 A | | 5/1985 | Atkinson et al. |
| 4,526,573 A | | 7/1985 | Lester et al. |
| 4,573,979 A | | 3/1986 | Blake |
| 4,583,531 A | | 4/1986 | Mattchen |
| 4,593,682 A | | 6/1986 | Heckele |
| 4,604,089 A | | 8/1986 | Santangelo et al. |
| 4,617,013 A | | 10/1986 | Betz |
| 4,646,722 A | | 3/1987 | Silverstein et al. |
| 4,680,026 A | | 7/1987 | Weightman et al. |
| 4,696,669 A | | 9/1987 | Menhusen |
| 4,708,717 A | | 11/1987 | Deane et al. |
| 4,776,840 A | | 10/1988 | Freitas et al. |
| 4,801,292 A | | 1/1989 | Watson |
| 4,881,523 A | | 11/1989 | Heckele |
| 4,911,148 A | | 3/1990 | Sosnowski et al. |
| 4,941,872 A | | 7/1990 | Felix et al. |
| 4,964,849 A | | 10/1990 | Robicsek |
| 4,979,497 A | * | 12/1990 | Matsuura et al. ............. 600/131 |
| 4,991,565 A | * | 2/1991 | Takahashi et al. ............ 600/123 |
| 5,100,377 A | | 3/1992 | Freitas et al. |
| 5,147,292 A | | 9/1992 | Kullas et al. |
| 5,170,774 A | | 12/1992 | Heckele |
| 5,199,950 A | | 4/1993 | Schmitt et al. |
| 5,201,908 A | | 4/1993 | Jones |
| 5,203,769 A | | 4/1993 | Clement et al. |
| 5,224,929 A | | 7/1993 | Remiszewski |
| 5,230,704 A | | 7/1993 | Moberg et al. |
| 5,231,989 A | | 8/1993 | Middleman et al. |
| 5,286,253 A | | 2/1994 | Fucci |
| 5,295,956 A | | 3/1994 | Bales et al. |
| 5,312,327 A | | 5/1994 | Bales et al. |
| 5,314,406 A | | 5/1994 | Arias et al. |
| 5,318,526 A | | 6/1994 | Cohen |
| 5,322,503 A | | 6/1994 | Desai |
| 5,328,467 A | | 7/1994 | Edwards et al. |
| 5,342,299 A | | 8/1994 | Snoke et al. |
| 5,354,267 A | | 10/1994 | Niermann et al. |
| 5,372,587 A | | 12/1994 | Hammerslag et al. |
| 5,378,234 A | | 1/1995 | Hammerslag et al. |
| 5,383,852 A | | 1/1995 | Stevens-Wright |
| 5,386,817 A | | 2/1995 | Jones |
| 5,397,321 A | | 3/1995 | Houser et al. |
| 5,429,596 A | | 7/1995 | Arias et al. |
| 5,437,636 A | | 8/1995 | Snoke et al. |
| 5,443,445 A | | 8/1995 | Peters et al. |
| 5,462,527 A | | 10/1995 | Stevens-Wright et al. |
| 5,484,402 A | | 1/1996 | Saravia et al. |
| 5,496,314 A | | 3/1996 | Eggers |
| 5,520,222 A | | 5/1996 | Chikama |
| 5,554,112 A | | 9/1996 | Walbrink et al. |
| 5,575,752 A | * | 11/1996 | Yabe et al. ................... 600/121 |
| 5,575,756 A | | 11/1996 | Karasawa et al. |
| 5,607,391 A | | 3/1997 | Klinger et al. |
| 5,609,573 A | | 3/1997 | Sandock |
| 5,709,698 A | | 1/1998 | Adams et al. |
| 5,792,098 A | | 8/1998 | Felix et al. |
| 5,842,973 A | | 12/1998 | Bullard |
| 5,855,549 A | | 1/1999 | Newman |
| 5,928,191 A | | 7/1999 | Houser et al. |
| 5,944,689 A | | 8/1999 | Houser et al. |
| 5,989,183 A | | 11/1999 | Reisdorf et al. |
| 5,993,410 A | | 11/1999 | Vincent et al. |
| 6,030,360 A | | 2/2000 | Biggs |
| 6,086,542 A | | 7/2000 | Glowa et al. |
| 6,110,103 A | | 8/2000 | Donofrio |
| 6,126,633 A | | 10/2000 | Kaji et al. |
| 6,174,280 B1 | | 1/2001 | Oneda et al. |
| 6,179,776 B1 | | 1/2001 | Adams et al. |
| 6,282,442 B1 | | 8/2001 | DeStefano et al. |
| 6,293,957 B1 | | 9/2001 | Peters et al. |
| 6,364,853 B1 | | 4/2002 | French et al. |
| 6,398,759 B1 | * | 6/2002 | Sussman et al. .............. 604/114 |
| 6,551,302 B1 | | 4/2003 | Rosinko et al. |
| 6,599,237 B1 | | 7/2003 | Singh |
| 6,623,445 B1 | | 9/2003 | Nelson et al. |
| 6,652,488 B1 | | 11/2003 | Cover et al. |
| 6,679,834 B2 | | 1/2004 | Stahl et al. |
| 6,712,757 B2 | | 3/2004 | Becker et al. |
| 6,712,759 B2 | | 3/2004 | Muller |
| 6,746,419 B1 | | 6/2004 | Arnett et al. |
| 6,770,050 B2 | | 8/2004 | Epstein |
| 6,811,544 B2 | | 11/2004 | Schaer |
| 6,863,668 B2 | | 3/2005 | Gillespie et al. |
| 6,907,879 B2 | | 6/2005 | Drinan et al. |
| 6,918,902 B2 | | 7/2005 | French et al. |
| 6,939,293 B2 | | 9/2005 | Conteas |
| 6,945,956 B2 | | 9/2005 | Waldhauser et al. |
| 7,025,759 B2 | | 4/2006 | Muller |
| 7,144,383 B2 | | 12/2006 | Arnett et al. |
| 7,522,955 B2 | | 4/2009 | Rontal |
| 8,016,753 B2 | * | 9/2011 | Sugita ........................... 600/156 |
| 2001/0025134 A1 | | 9/2001 | Bon et al. |
| 2002/0022829 A1 | | 2/2002 | Nagase et al. |
| 2003/0176769 A1 | | 9/2003 | Soble et al. |
| 2003/0181934 A1 | | 9/2003 | Johnston et al. |
| 2004/0059191 A1 | | 3/2004 | Krupa et al. |
| 2004/0267213 A1 | | 12/2004 | Knapp |
| 2005/0075621 A1 | | 4/2005 | Rontal |
| 2005/0080396 A1 | | 4/2005 | Rontal |
| 2005/0107853 A1 | | 5/2005 | Krespi et al. |
| 2005/0182353 A1 | | 8/2005 | Schmidberger et al. |
| 2005/0240147 A1 | | 10/2005 | Makower et al. |
| 2006/0004286 A1 | | 1/2006 | Chang et al. |
| 2006/0004323 A1 | | 1/2006 | Chang et al. |
| 2006/0009678 A1 | | 1/2006 | Jaffe et al. |
| 2006/0015009 A1 | | 1/2006 | Jaffe et al. |
| 2006/0015010 A1 | | 1/2006 | Jaffe et al. |
| 2006/0025652 A1 | | 2/2006 | Vargas |
| 2006/0041186 A1 | | 2/2006 | Vancaillie |
| 2006/0063973 A1 | | 3/2006 | Makower et al. |
| 2006/0069343 A1 | | 3/2006 | Rontal |
| 2006/0084910 A1 | | 4/2006 | Hoffman |
| 2006/0089534 A1 | | 4/2006 | Michel et al. |
| 2006/0095066 A1 | | 5/2006 | Chang et al. |
| 2006/0100481 A1 | | 5/2006 | Soble et al. |
| 2006/0111615 A1 | | 5/2006 | Danitz et al. |
| 2006/0210605 A1 | | 9/2006 | Chang et al. |
| 2006/0224103 A1 | | 10/2006 | Rontal |
| 2008/0167527 A1 | | 7/2008 | Slenker et al. |
| 2008/0249483 A1 | | 10/2008 | Slenker et al. |

FOREIGN PATENT DOCUMENTS

| | | |
|---|---|---|
| KR | 200289606 Y1 | 9/2002 |
| KR | 100439992 B1 | 7/2004 |
| WO | 9222238 A1 | 12/1992 |
| WO | 9505112 A1 | 2/1995 |
| WO | 2004112596 A1 | 12/2004 |
| WO | 2005006788 A1 | 1/2005 |

OTHER PUBLICATIONS

J. Christopher Post, MD et al., "Molecular Analysis of Bacterial Pathogens in Otitis Media with Effusion," JAMA, May 24-31, 1995, vol. 273, No. 20; 7 pgs.

(56) References Cited

OTHER PUBLICATIONS

E. M. Liederman, MD et al., "Analysis of Adult Otitis Media: Polymerase Chain Reaction Versus Culture for Bacteria and Viruses," Ann Otol Rhinol Laryngol 107:1998; pp. 10-16.

J. J. Aul, MD et al., "Comparative Evaluation and Culture and PCR for the Detection and Determination of Persistence of Bacterial Strains and DNAs in the Chinchilla Laniger Model of Otitis Media," Ann Otol Rhinol Laryngol 107:1998; pp. 508-513.

L. O. Bakaletz et al., "Blinded Multiplex PCR Analyses of Middle Ear and Nasopharyngeal Fluids from Chinchilla Models of Single- and Mixed-Pathogen-Induced Otitis Media," Clinical and Diagnostic Laboratory Immunology, Mar. 1998, pp. 219-224.

J.R. Dingman et al., "Correlation Between Presence of Viable Bacteria and Presence of Endotoxin in Middle-Ear Effusions," Journal of Clinical Microbiology, Nov. 1998, pp. 3417-3419.

J.W. Costerton, "Introduction to Biofilm," International Journal of Antimicrobial Agents 11 (1999); Dec. 2001; pp. 217-221.

J. Christopher Post, MD, PHD, "Direct Evidence of Bacterial Biofilms in Otitis Media," The Laryngoscope, Dec. 2001; pp. 2083-2094.

J.W. Costerson et al., "Battling loflims," Scientific American, Jul. 2001; pp. 75-81.

P.S. Mason et al., "Effect of Bacterial Endotoxin and Middle Ear Effusion on Ciliary Activity: Implications for Otitis Media," The Laryngoscope; Apr. 2002; pp. 676-680.

G.D. Ehrlich, PHD et al., "Mucosal Biofilm Formation on Middle-Ear Mucosa in the Chinchilla Model of Otitis Media," JAMA, Apr. 3, 2002, vol. 287, No. 13; pp. 1710-1715.

R.M. Donlan et al., "Biofilms: Survival Mechanisms of Clinically Relevant Microorganisms," Clinical Microbiology Reviews, Apr. 2002, pp. 167-193.

J. Cryer et al., "Evidence of Bactrial Biofilms in Human Chronic Sinusitis," Department of Otorhinolaryngology—Head and Neck Surgery, University of Pennsylvania Medical Center; 2004; pp. 155-158.

G.T. Rodeheaver, PHD, "Wound Cleansing, Wound Irrigation, Wound Disinfection," Chronic Wound Care: A Clinical Source Book for Healthcare Professionals, Third Edition, 2001; pp. 369-383.

J.N. Palmer MD, "Bacterial Biofilms: Do They Play a Role in Chronic Sinusitis?" Department of Otolaryngology—Head and Neck Surgery, Hospital of Pennsylvania, 2005; pp. 1193-1201.

A.Tripathi, MD et al., "Staphylococcal Exotoxins and Nasal Polyposis: Analysis of Systemic and Local Responses," American Journal of Rhinology, Jul.-Aug. 2005, vol. 19, No. 4; pp. 327-333.

J.E. Dohar, MD, MS et al., "Mucosal Biofilm Formation on Middle-Ear Mucosa in a Nonhuman Primate Model of Chronic Suppurative Otitis Media," The Laryngoscope, Aug. 2005; pp. 1469-1472.

B.J. Ferguson MD et al., "Demonstration of Biofilm in Human Bacterial Chronic Rhinosinusitis," American Journal of Rhinology, Sep.-Oct. 2005, vol. 19, No. 5, pp. 452-457.

L. Hall-Stoodley, PHD et al, "Direct Detection of Bacterial Biofilms on the Middle-Ear Mucosa of Children with Chronic Otitis Media," JAMA, Jul. 12, 2006, vol. 296, No. 2, pp. 202-211.

Z. Bendouah, BSC et al., "Biofilm Formation by *Staphylococcus aureus* and *Pseudomonas aeruginosa* is Associated with an Unfavorable Evolution After Surgery for Chronic Sinusitis and Nasal Polyposis," American Academy of Otolaryngology—Head and Neck Surgery Foundation; 2006; pp. 991-996.

PCT Search Report for PCT/US2008/058971 mailed Aug. 20, 2008, 11 pgs.

* cited by examiner

SYSTEMS AND METHODS FOR BIOFILM REMOVAL, INCLUDING A BIOFILM REMOVAL ENDOSCOPE FOR USE THEREWITH

CROSS-REFERENCE TO RELATED APPLICATIONS

This application is a continuation of U.S. application Ser. No. 11/680,781, filed Mar. 1, 2007, and entitled "Systems and Methods for Biofilm Removal, Including a Biofilm Removal Endoscope for Use Therewith", which is related to U.S. application Ser. No. 11/621,453, filed Jan. 9, 2007, and entitled "Surgical Systems and Methods for Biofilm Removal, Including a Sheath for Use Therewith," the teachings of which are incorporated herein by reference.

BACKGROUND OF THE INVENTION

Bacterial biofilms develop in variety of bodily cavities, including those of the ear, such as the middle ear, and of the nose, such as the frontal or maxillary sinuses, for example. Once bacterial growth has been established, the bacteria will often aggregate, stop dividing, and begin forming protective bacterial biofilm layers, or "slime layers," comprised of polysaccharide matrices.

The protective bacterial biofilm interferes with the body's natural immune response as well as traditional methods of treatment. In particular, the bacteria emit exotoxins, which incite the body's immune system to respond with white cells. However, the bacterial biofilm interferes with the efficacy of the white cells' ability to attack the bacteria. The biofilm can also act as a barrier against topical administration of antibiotics and other medicaments. Biofilm-forming bacteria also present obstacles to traditional, antibiotic treatments that act to kill dividing bacteria. In particular, the bacteria in a biofilm-forming state may have already ceased cell division, rendering such antibiotics largely ineffective.

For example, relative to chronic rhinosinusitis and other similar ailments, bacteria in the nose can be viewed as a continuum. Some bacterias (e.g., certain strains of *pseudomonas* and *staph aureus*) form robust biofilms. Others (e.g., h. flu) form relatively mild biofilms. The biofilms may or may not include or contain fungi. Each of these microbes has a somewhat different or complimentary inflammatory pathway and interacts with the host's immune system differently. For example, *staph aureus* produces a lipopolysaccharide matrix that acts as an antigen and causes a host response, as well as toxins (e.g., staph exotin A and B, toxic shock syndrome toxin 1 and 2) that can produce an antigenic and even hyperantigenic (hyperinflammatory) response. Other microbes can also produce inflammatory-inciting toxins.

Functional endoscopic sinus surgery (FESS) is a minimally invasive surgical procedure used to treat chronic rhinosinusitis, an infection of the sinuses. FESS opens up sinus air cells and sinus ostia (openings) with an instrument aided by an endoscope. The use of FESS as a sinus surgical method has now become widely accepted.

The purpose of FESS is typically to restore normal drainage of the sinuses, which requires ventilation through the ostia. In particular, a muco-ciliary transport process maintains a constant flow of mucus out of the sinuses with the hair-like cilia of a ciliated epithelium layer acting to direct the flow of mucus toward the ostia. Where there is insufficient ventilation or mucous transportation, infection and inflammation can result, a condition known as chronic rhinosinusitis. Chronic rhinosinusitis often develops from an infection where the maxillary and frontal sinuses meet near the nose or, occasionally, from a dental infection. Regardless, chronic rhinosinusitis causes the cilia to work less efficiently and causes the mucous membranes of the sinuses to become engorged, resulting in obstruction of the ostia. The ensuing lack of ventilation and drainage produce conditions which are ripe for bacterial infection, including biofilm-forming bacteria. As described above, such bacterial biofilms often interfere with effective treatment of bacterial infections, such as chronic rhinosinusitis.

With the foregoing background, it has been postulated that effective treatment of recurrent, chronic inflammatory diseases, such as chronic rhinosinusitis, requires therapies addressing associated bacterial infections and bacterial biofilms. To this end, needs exist for endoscopes and related methods of use for accomplishing these therapies.

SUMMARY OF THE INVENTION

Some embodiments relate to a method of removing bacterial biofilm from a target site of a human patient. A bacterial biofilm removal system is provided, the system including a biofilm removal endoscope. The endoscope has an insertion portion terminating at a working end. The insertion portion further forms an imaging channel terminating at a viewing window otherwise disposed at the working end. Further, the insertion portion forms an irrigation channel terminating at a nozzle otherwise carried at the working end. In this regard, the imaging and irrigation channels are permanently affixed relative to one another. The insertion portion is inserted into the patient, with the working end being disposed proximate the target site. In this regard, the target site includes a layer of bacterial biofilm adhered to a surface. The target site is imaged using the endoscope via the viewing window. A flow of fluid is dispensed toward the target site via the endoscope nozzle to mechanically remove a substantial portion of the layer of bacterial biofilm from the surface. In some embodiments, the insertion portion includes a flexible distal segment, with the method further including adjusting an attack angle of the nozzle relative to the target site by effectuating a bend in the distal segment. Other embodiments include aspirating removed bacterial biofilm via an aspiration channel provided with the endoscope.

Other embodiments relate to a bacterial biofilm removal system for removing bacterial biofilm from a target site of a human patient. The system includes a biofilm removal endoscope having a handle and an insertion portion. The insertion portion is adapted for bodily insertion and forms an imaging channel and an irrigation channel. The imaging channel terminates at a viewing window that otherwise facilitates imaging of the target site. The irrigation channel terminates at a nozzle projecting distally beyond the viewing window. With this construction, the endoscope is configured such that pressurized fluid delivered through the irrigation channel is directed by the nozzle to impinge upon a layer of bacterial biofilm at the target site. In some embodiments, the insertion portion further forms an aspiration channel terminating at a distal inlet for aspirating removed bacterial biofilm.

DETAILED DESCRIPTION OF THE INVENTION

Figure 1:
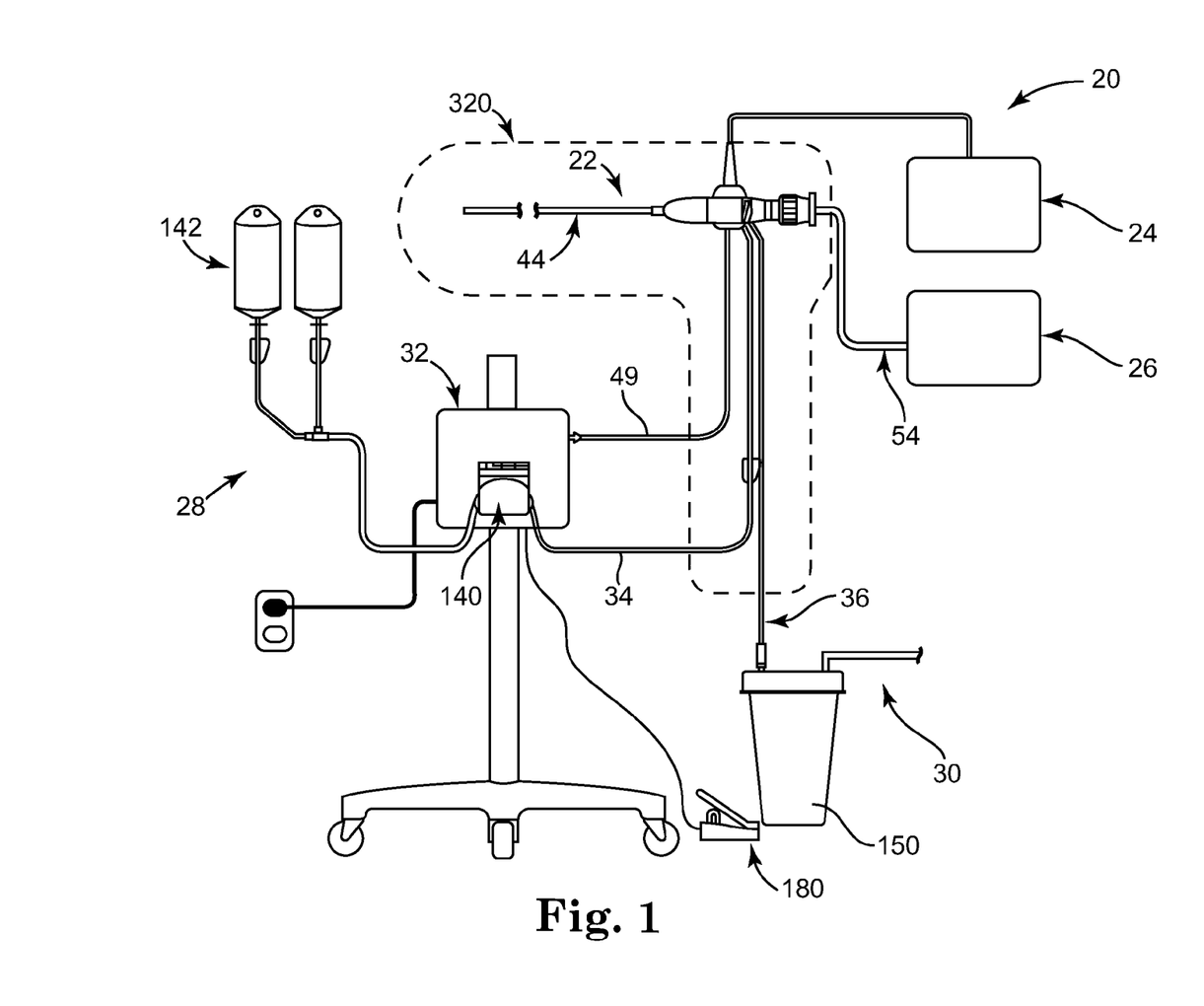
FIG. 1 is a schematic illustration of a surgical biofilm removal system in accordance with aspects of the present disclosure.

A surgical bacterial biofilm removal system 20 according in accordance with principles of the present disclosure shown in FIG. 1. The system 20 includes a biofilm removal endoscope 22, a light source 24, an imaging device 26, a fluid source 28, a vacuum source 30 (referenced generally), and a controller 32. In general terms, the biofilm removal endoscope 22 operates in conjunction with the light source 24 and the imaging device 26 to facilitate visualization of a surgical area, akin to conventional endoscopes. In addition, the fluid source 28 provides fluid, or irrigant, to the biofilm removal endoscope 22, for example via a fluid connector 34 (e.g., tubing). Conversely, the vacuum source 28 provides vacuum flow, or aspiratory flow, to the endoscope 22, for example via a vacuum connector 36 (e.g., tubing). The controller 32 controls aspects of operation of the system 20 in performing a bacterial biofilm removal procedure, and is indicated as being generally associated with the biofilm removal endoscope 22 and the fluid source 28.

Figure 2:
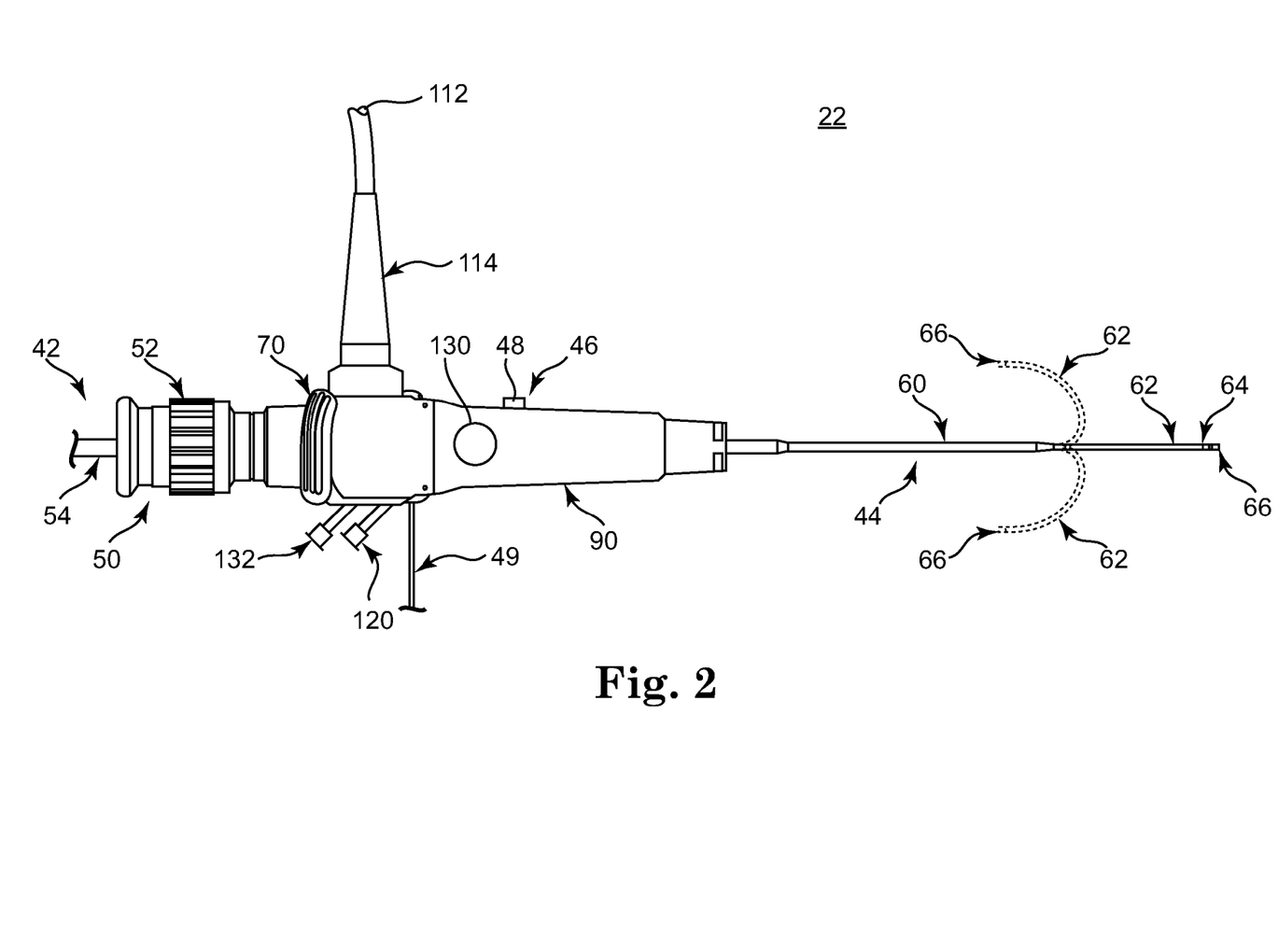
FIG. 2 is a side view of a biofilm removal endoscope useful with the system of FIG. 1.

The biofilm removal endoscope 22 (or "endoscope") is shown in greater detail in FIG. 2, and includes various conventional components otherwise useful in imaging internal bodily structures. In general terms, for example, the endoscope 22 includes a handle 40, an imaging assembly 42, and an insertion portion 44. The imaging assembly 42 is maintained by, and extends proximally from, the handle 40, whereas the insertion portion 44 extends distally from the handle 40. In this regard, the insertion portion 44 is sized for bodily insertion and forms one or more channels or lumens (hidden in FIG. 2) that facilitate target site imaging as well as biofilm removal as described below.

The handle 40 is adapted to promote convenient handling of the endoscope 22 by a user in performing a biofilm removal procedure, and thus can assume a variety of shapes and sizes. The handle 40 maintains the imaging assembly 42 and the insertion portion 44, as well as other internal components, as described below. For example, the handle 40 maintains a trigger assembly 46 (referenced generally) adapted to allow user-controlled activation and deactivation of irrigant fluid flow to the biofilm removal endoscope 22. The trigger assembly 46 can assume a variety of forms and generally includes a moveable trigger 48, a sensor (not shown), and a connector 49. The sensor senses movement of the trigger 48 (e.g., when depressed by a user), with the connector 49 is electronically connected to the controller 32 (FIG. 1) that in turn signaling information sensed by the sensor. Thus, the connector 49 prompts delivery of irrigant (or prompts attenuation in the delivery or irrigant). The connector 49 can assume a variety of forms, such as tubing, wire(s), wireless connector, etc.

The imaging assembly 42 can be of a conventional construction and generally includes an eye piece 50 and a focus ring 52, and a connecting assembly 54 (referenced generally). The eye piece 50 provides imaging information generated at a target site (as described below). "Imaging," "adapted to image," and similar language should be understood to be inclusive of all direct visualization through the optical components of the endoscope 22, as well as the electronic visualization and/or data analysis via electronic imaging, for example using the imaging device 26 (FIG. 1) or other electronics. With this in mind, the focus ring 52 is disposed about the eye piece 50, and is operable to bring images, or image data into focus. The connection assembly 54 is adapted to establish an electronic connection between the imaging assembly 42 and the imaging device 26 as is known in the art. Alternatively, the imaging assembly 42 can assume a variety of other forms, and the eye piece 50 and/or the focus ring 52 can be eliminated.

The insertion portion 44 has an elongated configuration sized for minimally invasive, bodily insertion. In this regard, the insertion portion 44 can be comprised of one or more structures affixed to one another, or can be a singular, homogenous body. Regardless, the insertion portion 44 is generally defined by a proximal segment 60 and a distal segment 62. The proximal segment 60 extends from the handle 40, whereas the distal segment 62 extends from the proximal segment 60 and terminates at a tip 64 forming a working or distal end 66. Various features of the endoscope 22 otherwise facilitated at the working end 66 are described below. In some embodiments, the proximal segment 60 is rigid or substantially rigid, whereas the distal segment 62 is flexible or articulatable in allowing for user-controlled movement of the tip 64 relative to the handle 40. For example, the distal segment 62 can include one or more bodies each formed of a flexible material, a series of links, vertebrae, or is otherwise suited to facilitate selective bending thereof. In this regard, the endoscope 22 includes components for articulating the distal segment 62, including those known to one of skill (e.g., pull wires), and includes a control assembly 70 (referenced generally) maintained by the handle 40 and operable by a user to effectuate bending of the distal segment 62 and thus "aiming" of the tip 64/working end 66 in a desired direction. With this construction, then, the distal segment 62 is articuable or bendable in various directions, as shown in phantom in FIG. 2. Alternatively, and as described in greater detail below, the insertion portion 44, including the distal segment 62, can have a more rigid configuration and/or can be formed of a malleable material allowing a user to manipulate the distal segment 62 to desired bend angle(s) and then rigidly maintain this shape during use.

Figures 3A, 3B, 3C:
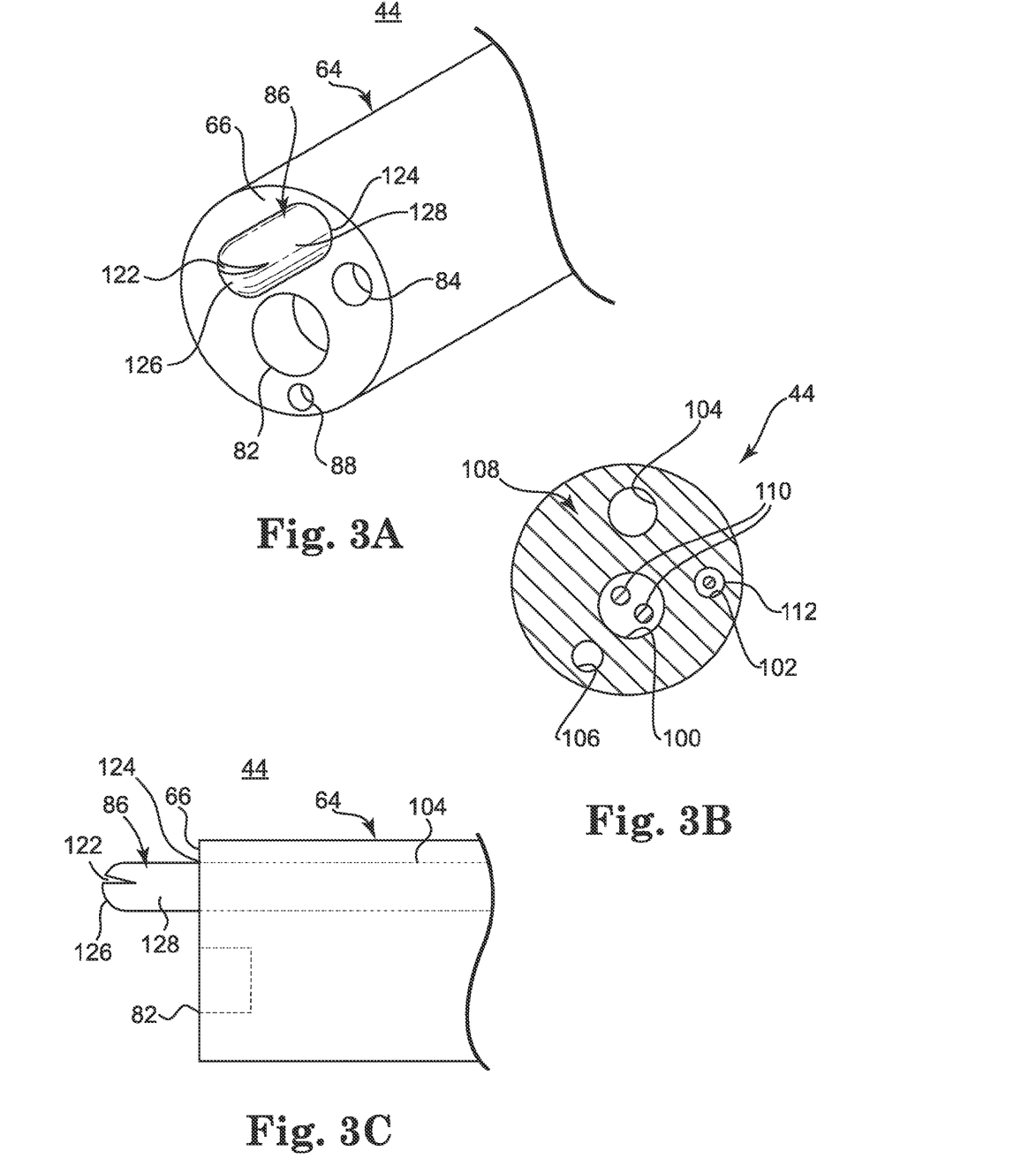
FIG. 3A is an enlarged, perspective view of a distal tip portion of the biofilm removal endoscope of FIG. 2.
FIG. 3B is a cross-sectional view of the tip of FIG. 3A.
FIG. 3C is a side view of the tip of FIG. 3A.

Additional features of the endoscope 22, and in particular the insertion portion 44, are shown in FIGS. 3A and 3C that otherwise illustrates the tip 64 in greater detail. The working end 66 is generally defined as a radial or transverse face of the insertion portion 44. With this in mind, the insertion portion 44 includes a viewing window 82, an illumination port 84, a nozzle 86, and an aspiration inlet 88. The viewing window 82 is formed in the working end 66, and is of a type known in the art. In particular, the viewing window 82 facilitates acquisition of imaging data or information, and is thus optically connected to the imaging assembly 42 (FIG. 2) as described below. The illumination port 84 is similarly formed in the working end 66, and serves as a point from which light is emitted from the endoscope 22. In this regard, the illumination port 84 is optically connected to the light source 24 (FIG.

1) as described below. The nozzle 86 projects distally from the working end 66, and is adapted to dispense pressurized fluid or irrigant toward a target site. Finally, the aspiration inlet 88 is formed in the working end 66, and promotes aspiration or evacuation of fluid and other materials from the target site during use.

Each of the components 82-88 are connected to corresponding other components of the system 20 (FIG. 1) via one or more channels formed by the insertion portion 44. For example, and with reference to FIG. 3B, the insertion portion 44 includes an imaging channel 100, an illumination channel 102, a fluid channel 104, and an aspiration channel 106. In some embodiments, the channels 100-106 are provided as lumens formed in an integral homogenous body 108. Alternatively, one or more of the channels 100-106 can be defined by a tube or similar structure that is assembled to one or more other bodies otherwise defining the remaining channels 100-106. Regardless, the channels 100-106 are permanently affixed relative to one another, and thus are each provided as part of the biofilm removal endoscope 22.

With combined reference to FIGS. 2-3B, the imaging channel 100 optically connects the viewing window 82 to the imaging assembly 42. As is conventionally known, then, the imaging assembly 42 can acquire image information at the working end 66 via the viewing window 82 and the imaging channel 100. In this regard, the insertion portion 44 can include fiber optic strands or bundles 110 (schematically illustrated in FIG. 3B) disposed within the imaging channel 100 and extending through the handle 40 for establishing an optical connection between the viewing window 82 and the imaging assembly 42, as is known.

The illumination channel 102 optically connects the illumination port 84 with the light source 24 (FIG. 1). In this regard, an optical fiber bundle 112 (schematically illustrated in FIG. 3B) can be disposed within the illumination channel 102, extending through the insertion portion 44, and to the handle 40. With this construction, the endoscope 22 can further include a light post 114 (FIG. 2) or similar structure that connects the encased optical fibers 112 with the light source 24. Alternatively, any other construction appropriate for delivering illumination to the working end 66/illumination port 84 is also acceptable. Further, two or more of the illumination port 84 and the illumination channel 102 can be provided.

The fluid channel 104 is fluidly connected to the nozzle 86, and extends through the insertion portion 44. As described below, the fluid channel 104 is a lumen defined by the insertion portion body 108 in some embodiments. With this approach, the handle 40 internally maintains tubing (not shown) fluidly connected to the lumen. Alternatively, the fluid channel 104 can be a flexible bendable tube extending along the insertion portion 44 and into the handle 40. Regardless, the handle 40 includes or forms an irrigation port 120 (FIG. 3A) adapted for fluid connection to the irrigant tubing 34 (FIG. 1).

With specific reference to FIGS. 3A and 3C, the nozzle 86 forms an opening 122 through which fluid irrigant delivered to the nozzle 86 is dispensed. The nozzle 86 can assume a variety of forms, but in some embodiments is configured to generate a fan-like spray pattern, and is rotatable maintained by, or assembled to, the working end 66. As a point of reference, in accordance with some aspects of the present disclosure, the biofilm removal endoscope 22 is provided to mechanically disrupt biofilms with a fluid stream as produced through the nozzle 86. In this regard, while the nozzle 86 can be a simple orifice-type nozzle, it has surprisingly been found that a fan spray-type nozzle configuration can provide unexpected benefits in the context of biofilm removal. An orifice nozzle produces a focused stream approximately equal to the diameter of the orifice. This, in turn, produces mechanical disruption at a relatively small area of tissue during use. To effectuate biofilm removal over a larger area, then, an orifice-type nozzle likely must then be articulated in space to treat other areas. With the one configuration of FIGS. 3A and 3C, however, the nozzle 86 is a fan spray-type nozzle that produces mechanical disruption on a "line" of tissue. When the nozzle 86 is rotated about its axis (as described below), this line can then sweep out a comparatively larger area of tissue.

With the above in mind, the nozzle 86 can be tubular-type body defining a base end 124 (referenced generally) assembled to the working end 66, and an opposite, leading, hemispherical end 126 at which the opening 122 is made in the form of a V-cut. In some embodiments, the V-cut opening 122 is formed to extend along a side 128 of the nozzle 86 so as to produce a side-looking spray pattern (and thus cover more area with rotation of the nozzle 86 as described below). Alternatively, the V-cut opening 122 can be centrally formed relative to an axis of the nozzle 86. Regardless, the nozzle 86 is assembled to the working end 66 such that the leading end 126 of the nozzle 86 projects distally beyond the working end 66 such that the spray pattern generated by or through the opening 122 is not impacted by the working end 66.

As indicated above, in some embodiments, the nozzle 86 is assembled so as to be movable relative to the working end 66. In this regard, the nozzle 86 can be pivotably attached to the working end 66, with the endoscope 22 further including components for effectuating user-controlled rotation of the nozzle 86. For example, as schematically illustrated in FIG. 3C, the fluid channel 104 can be (or can have disposed therein) a rigid yet bendable tube (e.g., thin metal tubing) affixed to the nozzle 86, that is rotatably assembled relative to a remainder of the insertion portion 44 and extends into the handle 40 (FIG. 2). With this construction, upon rotation of the fluid channel/tube 104 (e.g., a geared interface (not shown) provided at a user-activated nozzle controller 130 maintained by the handle 40), the nozzle 86 will rotate. A variety of other configurations capable of effectuating user-controlled rotation of the nozzle 86 are also acceptable. Alternatively, the nozzle 86 can be permanently affixed relative to the working end 66, and thus not rotatable relative to a remainder of the insertion portion 44.

Returning to FIGS. 2-3B, the aspiration channel 106 is fluidly connected to the aspiration inlet 88, and extends through the insertion portion 44. As with the fluid channel 104 described above, the aspiration channel 106 can be defined by a tube extending through the insertion portion 44 and into the handle 40, or can be a lumen formed by the insertion portion body 108, with the handle 40, in turn, maintaining a separate tube (not shown) that is fluidly connected to the lumen. As shown in FIG. 2, the handle 40 further includes or forms an aspiration port 132 that is fluidly connected to the aspiration channel 106. The aspiration port 132 is adapted for fluid connection to the vacuum source 30 (FIG. 1), for example via the vacuum tubing 36 (FIG. 1) as previously described. Regardless, the aspiration channel 106 facilitates aspiration or removal of fluid to the vacuum source 30 via the aspiration inlet 88.

With the above explanations in mind, upon final assembly, the biofilm removal endoscope 22 is constructed to perform conventional endoscopic imaging as well as to deliver a focused, pressurized spray or flow of fluid from the insertion portion 44 via the nozzle 86. In this regard, the supply of irrigation fluid is provided via the fluid channel 104. The spatial, angular orientation of the tip 64, and thus of the nozzle 86, can be selected and altered by a user via the control assembly 70. Thus, an "angle of attack" of the nozzle 86 relative to the biofilm target site can be adjusted by the user as desired. Further, the endoscope 22 can facilitate evacuation of the removed biofilm (as well as other liquid or matter) from the target site via the aspiration inlet 88/aspiration channel 106.

Returning to FIG. 1, other components of the system 20 can assume a variety of forms. For example, the light source 24 is provided to the endoscope 22 that in turn directs the emitted light to the illumination port 84 in illuminating an internal bodily structure or other target site being imaged, with associated images, or image data, being transmitted back from the working end 66 (and in particular the viewing window 82) and to the imaging device 26 via the endoscope 22. With this in mind, the imaging device is optionally an image sensor, such as a video camera, display, and/or other imaging electronics, including those typically used in association with endoscopic procedures. The imaging device 26 can be a standalone component, or can be linked to the controller 32. Regardless, and as is conventionally known, the imaging device 26 and the endoscope 22 are used for imaging before, during, and/or after a biofilm removal procedure using the endoscope 22.

The fluid source 28 can include a pump 140 connected to a reservoir 142. In some embodiments, the pump 140 is a peristaltic pump, such as those typically used in association with surgical procedures, the pump 140 serving to pressurize a flow of fluid from the reservoir 142 to the endoscope 22 as described below. The reservoir 142 can include one or more IV bags, for example filled with an irrigant, including the irrigating fluids described in U.S. patent application Ser. No. 11/431,495 entitled "Biofilm Extracellular Polysaccharide Solvating (EPS) System," filed May 10, 2006, the contents of which are incorporated herein by reference. In some embodiments, the irrigant includes medicaments, including those adapted to interfere with bacterial biofilm regrowth, surfactants, gels, anti-microbials, steroids, growth hormones, chemicals for reducing biofilm adhesion force, and others.

The fluid source 28 is connected to the endoscope 22 via the fluid connector 34, which in some embodiments is a tubing set. For example, the fluid connector 34 can be in fluid communication with (or formed as part of) the fluid channel 104 (FIG. 3B), such as via the irrigation port 120 (FIG. 2). Further, the fluid connector 34 can include an auxiliary inlet or port (not shown) for introducing medicaments into irrigant (not shown) flowing form the fluid source 28, for example the medicaments described above.

The vacuum source 30 (referenced generally) is adapted to provide an aspiratory or vacuum flow to the endoscope 22 via the vacuum connector 36. The vacuum source 30 can include a canister 150 fluidly connecting a source of negative pressure (not shown) to the vacuum connector 36. The vacuum connector 36 is placed into fluid communication with, or if formed as part of, the aspiration channel 106 (FIG. 3B) and the source of negative pressure 30. To the end, the aspiration port 130 can serve to fluidly connect the vacuum connector 36 with the aspiration channel 106. In this manner, the aspiration inlet 88 (FIG. 3A) is in fluid communication with the vacuum source 30 such that an aspiratory flow can be "pulled" through the aspiration channel 106. Additionally, and in some embodiments, the canister 150 serves as a disposal means, such as a disposal tank, for collecting debris and other matter aspirated during use of the biofilm removal endoscope 22, including those generally used in surgical procedures.

As previously referenced, the controller 32 controls operation of the system 20 and is designed as being physically associated with the fluid source 28, although the controller 32 is optionally a standalone device or physically associated with any of the other system components. The controller 32 can assume a variety of forms capable of performing various functions and can include a microchip, a memory, and/or other appropriate controller electronics.

The controller 32 is placed in communication with the biofilm removal endoscope 22 and the fluid source 28. The controller 32 can be electronically connected to the endoscope 22 via the connector 49 that is otherwise associated with the trigger assembly 46 (FIG. 2). The controller 32 can also be placed in direct or indirect communication with the fluid source 28 and/or the vacuum source 30 via wiring or alternative means as appropriate, for example using wireless transmitters and receivers. Regardless, in some embodiments, actuation of the trigger assembly 46 sends a signal to the controller 32 that, in turn, activates the fluid source 28 to provide a flow of irrigant to the endoscope 22 as desired. In some embodiments, the controller 32 can further control operations of the vacuum source 30, either directly or indirectly. Along these lines, in other configurations, the controller 32 can be programmed or adapted to operate the system 20 according to a variety of desired irrigation and/or aspiration profiles, including ramp actuation, time delays, varied flow patterns, and others. For example, in some embodiments, the system 20 can further include a foot switch 180 or similar device electronically connected to the controller 32, with the foot switch 180 being operated by a user (not shown) to control operation of the endoscope 22, the fluid source 28, and/or the vacuum source 30. In other embodiments, the foot switch 180 can be directly connected to the vacuum source 30 for controlling operation thereof.

Figure 4:
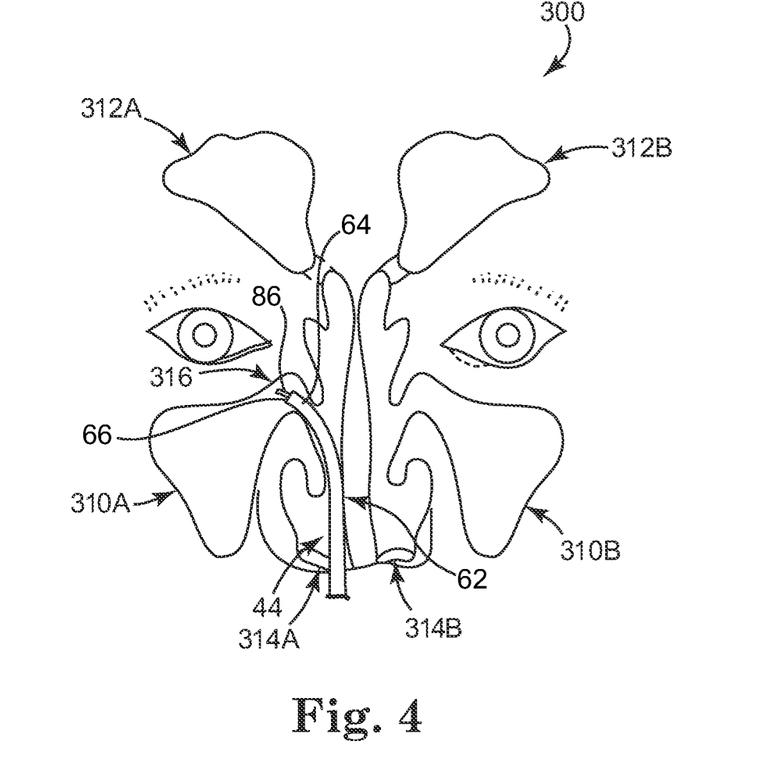
FIG. 4 illustrates methods of removing bacterial biofilm relative to a human anatomy in accordance with principles of the present disclosure.

The system 20 can be employed to perform a variety of procedures at various anatomical locations of the patient. By way of but one example, FIG. 4 illustrates internal bodily structures 300 of the patient, including sinus cavities such as the maxillary sinuses 310a, 310b, and front sinuses 312a, 312b, which are accessed through nares 314a, 314b. It should be noted that external features of the patient, including the nares 314a, 314b, are shown in dashed lines. For some procedures in which the system 20 is useful (e.g., a patient suffering from chronic rhinosinusitis), a first target site 316 can be designated in association with a surface of the maxillary sinus 310a for description of a surgical methodology for substantially removing a layer of biofilm (not shown). It should be understood, however, that similar principles apply across embodiments, including a variety of target sites associated with a variety of internal bodily structures, such as sinus cavities (e.g., the maxillary, frontal sphenoid, etc.), cavities of the ear (the middle ear and others), etc. With this in mind, in some embodiments, the first target site is ciliated epithelium of the maxillary sinus 310a that has an associated layer of bacteria and associated biofilm (not shown). In other embodiments, the target site 316 is an artificial structure (not shown), such as sinus packing or a stent covered with a layer of bacterial biofilm, for example.

With combined reference to FIGS. 1 and 4, use of the system 20 in removing bacterial biofilm from the target site 316 includes connecting the biofilm removal endoscope 22 to the light source 24 and the imaging device 26 as is conventionally known. The fluid source 28 and the vacuum source 30 are similarly connected to the endoscope 22 as described above. A sterile barrier 320 (illustrated schematically in FIG. 1), such as sheeting or others commonly used in surgical and/or endoscopic procedures, is positioned around the endoscope 22 and the patient in some embodiments to help maintain a sterile operating environment.

The insertion portion 44 is then inserted into the patient and directed toward the target site 316. In this regard, the imaging device 26 (along with the light source 24) are employed in properly positioning the insertion portion 44 relative to the target site 316. Along these same lines, a functional endoscope sinus surgery (FESS) can also be performed prior to, or concurrently with, delivery of the insertion portion 44.

As referenced above, although some embodiments of acting upon a target site to remove a layer of biofilm are described with reference to the maxillary sinus 310a and the target site 316, it will be understood the biofilm removal at other target sites and/or cavities, including sinus cavities or cavities of the middle ear (not shown), can proceed in a substantially similar manner. With this in mind, the biofilm removal endoscope 22 is initially operated to image the target site 316 (or other internal bodily structure) prior to, during, and/or following operation of the system 20 in performing a biofilm removal procedure.

As shown in FIG. 4, the insertion portion 44 of the endoscope 22 is inserted into the maxillary sinus 310a via the naris 314a, with the tip 64/working end 66 being directed toward or proximate the target site 316. In this regard, the imaging device 26 and the endoscope 22 are operated to acquire images prior to, during, or after insertion of the insertion portion 44 in order to assist the practitioner in guiding and/or "aiming" the working end 66 (and thus the nozzle 86) at the target site 316.

The distal segment 62 is then selectively bent or articulated by the user (via the control assembly 70) to "aim" the working end 66/nozzle 86 in a desired direction relative to the target site 316 and/or to facilitate directing of the insertion portion 44 into the maxillary sinus 310a. As the tip 64 approaches the target site 316, the distal segment 62 is further articulated to address an angle of attack defined by the working end 66, and in particular the nozzle 86, relative to the target site 316. In this regard, the practitioner can evaluate whether the working end 66/nozzle 86 is promptly "aimed" or otherwise disposed relative to the target site 316 via operation of the endoscope 22/imaging device 26. In some embodiments, the practitioner can identify the target site 316 by observing the presence/location of the layer of biofilm, for example by evaluating images displayed on the imaging device 26.

Once positioned as desired, the practitioner then prompts delivery of a pressurized flow of irrigant to the target site 316 to effectuate removal or eradication of a substantial amount of the bacterial biofilm from the target site 316 by interfacing with the trigger assembly 46. In response to this interface or actuation, a signal is sent to the controller 32 that in turn prompts activation of the fluid source 28 to provide the flow of irrigant through the fluid channel 104 (FIG. 3B) and thus the nozzle 86. It is contemplated that the flow of irrigant will be directed through the nozzle 86 at a variety of flow rates according to various embodiments, including a flow rate from about 2 mL/sec to about 12 mL/sec. In some embodiments, the system 20 is adapted to cause pulse flow through the nozzle 86, and in others a substantially continuous flow, and in still others, a flow pattern other than pulsed or substantially continuous flow.

The flow or irrigant dispensed from the nozzle 86 directly impinges upon, or otherwise directly strikes, the target site 316 to mechanically agitate and remove a substantial portion, or substantially all, of the biofilm. In other words, the nozzle 86 is able to be aimed directly at the target site 316 as previously described when sufficiently accessed by the insertion portion 44, such that a mechanical "scrubbing" action is accomplished. It should be noted that the pressure and/or flow rate of the irrigant is selected to promote mechanical removal of the biofilm without substantial damage to underlying tissue, such as a ciliated epithelium layer. For example, a pressure of less than about 50 psi can be selected, although other pressures are also acceptable.

With continued flow of the pressurized irrigant from the nozzle 86, the practitioner periodically and/or continuously rotates the nozzle 86 as previously described. With this approach, the nozzle 86 effectuates a swept fan spray pattern across the target site 316. Notably, with this swept spray pattern, the ability to accurately locate the working end 66/nozzle 86 relative to the target site 316 is of less concern in that a relatively large surface area can be acted upon by the pressurized irrigant delivered from the nozzle 86. Alternatively, however, the nozzle 86 can assume a wide variety of other configurations and/or the ability to rotate the nozzle 86 relative to the working end 66 need not be provided.

In some embodiments, aspiration of removed bacterial biofilm, bacteria, mucous, secretions, dead tissue, or other unwanted matter is accomplished using the aspiration inlet 88 (FIG. 3A), for example during and/or after dispensing the irrigant against the target site 316. The biofilm removal endoscope 22 is operated to selectively or continuously activate the vacuum source 30 in response to the user operating the trigger assembly 46 and/or the foot switch 180, for example concurrently with irrigation and/or with some time differential (for example, before or after irrigation). The unwanted matter is removed from the target site 316 and can be directed to the biological collection canister 150 otherwise associated with the vacuum source 30.

The systems and methods described above are highly useful in surgically treating various maladies associated with multiple different and anatomical locations or target sites. For example, in addition to sinus and inner ear target sites, the systems and methods of the present disclosure can be used to treat target site(s) in patient's lungs (e.g., cystic fibrosis and the respiratory epithelium of the lungs), urological and/or gynecological (e.g., urinary tract infections), etc.

The system and methods of the present disclosure provide a marked improvement over previous techniques and devices used to treat various ailments, such as chronic rhinosinusitis. By effectuating biofilm eradication using a focused, pressurized fluid, a more complete treatment is provided to the patient on a minimally invasive basis. Further, with sinus and other applications, drainage pathway(s) are restored, ventilation of the treatment site is provided (thus minimizing opportunities for biofilm regrowth), and other functional and endoscopic sinus surgery treatments can be provided (e.g., topical application of medicaments, irrigation, etc.).

In view of the above, a method for eradicating bacterial biofilm from a target site within an internal bodily cavity using the biofilm removal endoscope 22 is provided according to some embodiments. In this regard, while the endoscope 22 has been described as having the flexible distal segment 62, in other embodiments, a more rigid construction can be provided.

Figure 5A:
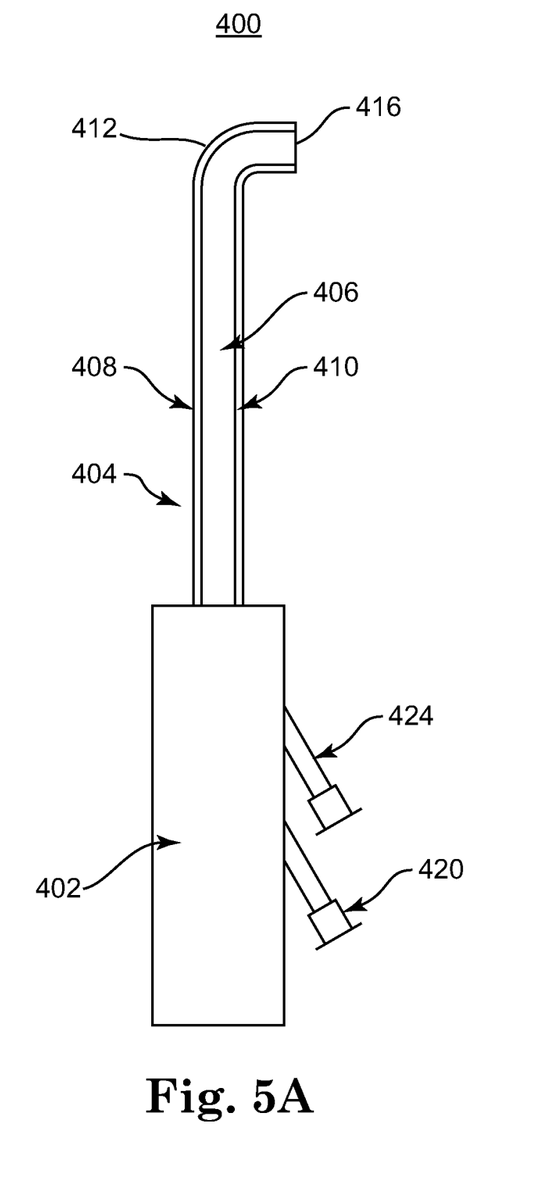
FIG. 5A is a simplified top view of another biofilm removal endoscope in accordance with principles of the present disclosure.
Figure 5B:
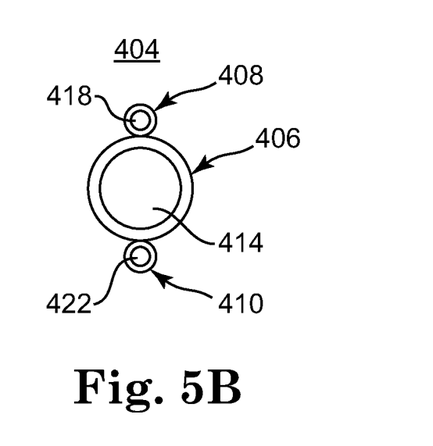
FIG. 5B is an end view of an insertion portion of the biofilm removal endoscope of FIG. 5A.

For example, FIGS. 5A and 5B schematically illustrate another embodiment biofilm removal endoscope 400 useful with the system 20 (FIG. 1) described above. The endoscope 400 is substantially similar to the biofilm removal endoscope 22 (FIG. 1) with corresponding components including a handle 402 and an insertion portion 404. Other components (e.g., imaging assembly) are not shown in FIG. 5. Regardless, the insertion portion 404 is relatively rigid, and is comprised of first, second, and third tubes 406-410. The tubes 406-410 are permanently affixed to one another, and collectively define the insertion portion 404 to have one or more bends 412. A rigid construction of the insertion portion 404 is such that the bend(s) 412 is independently maintained and will not change during normal use of the endoscope 400. Thus, a degree and location of the bend(s) 412 is predefined for use of the biofilm removal endoscope 400 in performing a particular procedure.

With the above in mind, the first tube 406 defines imaging and illumination channel(s) 414 (referenced collectively) within which necessary optical components (not shown) are maintained for performing endoscopic imaging of a target site as previously described. Thus, for example, the first tube 406 can terminate at a viewing window (not shown) and an illumination port (not shown) at a distal working end 416 of the insertion portion 404.

The second tube 408 is affixed to the first tube 406, and forms a fluid channel 418 adapted for delivering irrigant. In this regard, the insertion portion 404 further includes a nozzle (not shown) akin to the nozzle 86 (FIG. 3A) previously described that is otherwise fluidly connected to the second tube 408 and projects distally from the working end 416. An opposite end of the second tube 408 is fluidly connected to and/or forms an irrigation port 420 adapted for fluid connection to the fluid source 28 (FIG. 1).

The third tube 410 is similarly affixed to the first tube 406, and forms an aspiration channel 422 adapted to establish a fluid connection between an aspiration inlet 422 formed at the working end 416 and the vacuum source 30 (FIG. 1). In this regard, the third tube 410 can be connected to and/or form an aspiration port 424 that otherwise is available for fluid connection to the vacuum source 30.

The biofilm removal endoscope 400 can be used in conjunction with the biofilm removal system 20 (FIG. 1) as previously described. In this regard, the nozzle (not shown) can be rotatably assembled relative to the working end 416 of the insertion portion 404, or can be rigidly affixed. Regardless, desired placement of the working end 416, and in particular the nozzle relative to the target site can be visually confirmed by the practitioner via the imaging capabilities of the endoscope 400. Once desirably positioned, pressurized fluid delivered from the nozzle is employed to effectuate biofilm removal followed by and/or concurrently with, aspiration of removed material.

Figures 6A, 6B, 6C:
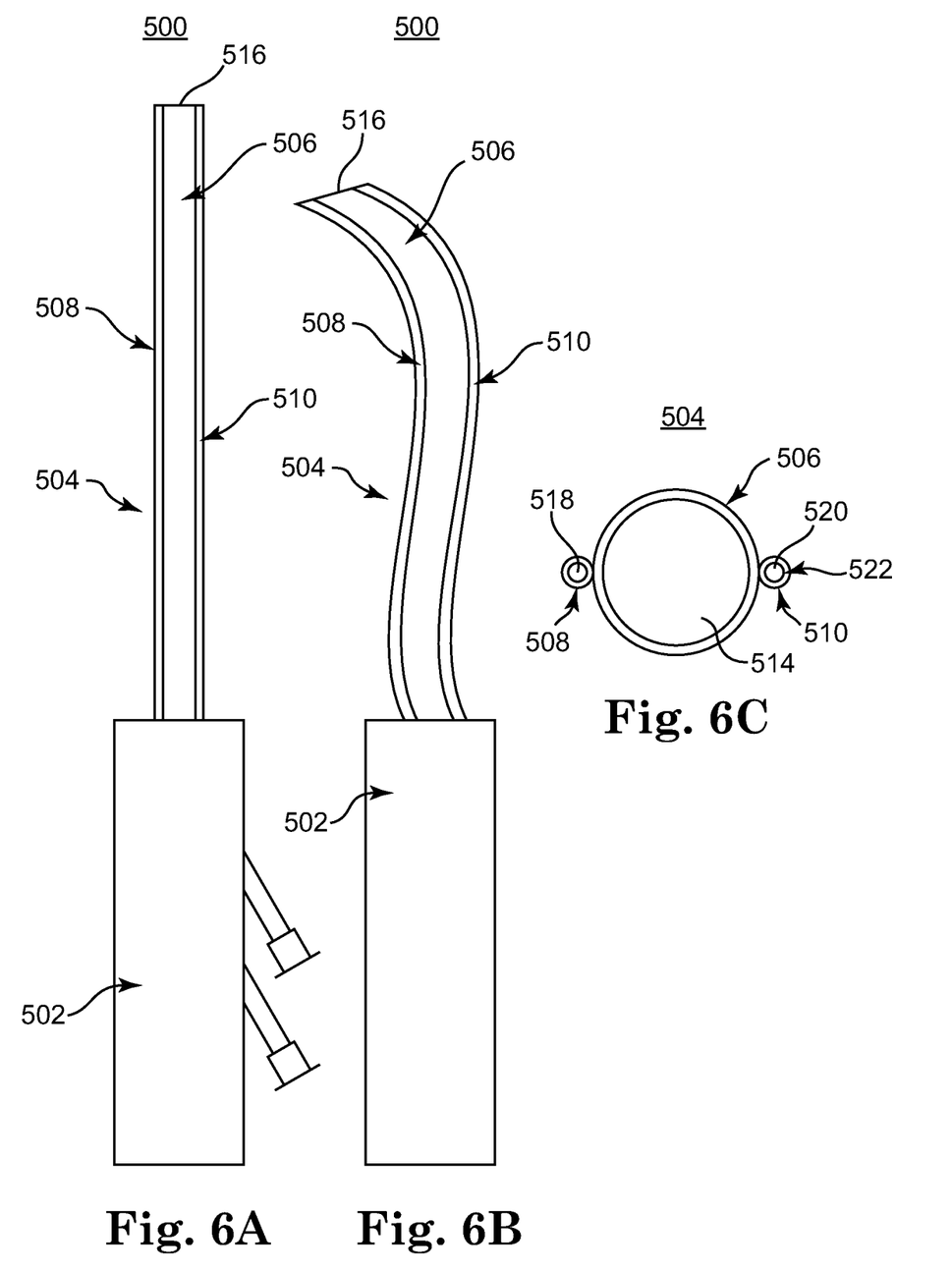
FIGS. 6A and 6B are simplified top views of another biofilm removal endoscope in accordance with principles of the present disclosure in two different states.
FIG. 6C is an end view of an insertion portion of the biofilm removal endoscope of FIG. 6A.

FIGS. 6A-6C illustrate another embodiment biofilm removal endoscope 500 useful with the system 20 (FIG. 1). As with previous embodiments, the endoscope 500 includes a handle 502 and an insertion portion 504. The insertion portion 504 is comprised of first, second, and third tubes 506-510, each formed of a rigid yet malleable material (e.g., thin walled metal tubing). With this construction, the insertion portion 504 can be manipulated by a practitioner to assume a variety of desired bends at desired locations, as shown, for example, by comparison of FIGS. 6A and 6B, with the insertion portion 504 independently maintaining the so-formed bend(s) during use. Similar to the biofilm removal endoscope 400 of FIG. 5, the first tube 506 forms a channel(s) 514, adapted to maintain various optical components necessary for effectuating endoscopic imaging of a target site. In this regard, the insertion portion 504 can include requisite optical components at a working end 516 thereof and optically connected to the first tube 506 including, for example, the viewing window (not shown), and an illumination port (not shown).

The second tube 508 forms a fluid channel 518 adapted to deliver irrigant to a nozzle (not shown) fluidly connected thereto and projecting from the working end 516. The third tube 510 forms an aspiration channel 520 adapted to aspirate fluid and other matter from the working end 516, for example via an aspiration inlet 522. Regardless, the tubes 506-510 are permanently affixed relative to one another.

During use, the biofilm removal endoscope 500 operates in connection with the system 20 in a manner highly similar to that previously described. With the embodiment of FIGS. 6A-6C, however, prior to use, the insertion portion 504 is bent by a practitioner to a desired shape commensurate with the procedure to be performed. The working end 516 is then delivered to the target site, based upon reference to images endoscopically acquired.

Although the endoscopes 20 (FIG. 1), 400 (FIGS. 5A and 5B), and 500 have been described as each including irrigation and aspiration channels, in other embodiments, one of the channels can be removed from the endoscope, and provided as part of a separate device. Thus, for example, in other embodiments, the biofilm removal endoscope in accordance with principles of the present disclosure includes requisite components/channels for performing endoscope imaging (e.g., an imaging channel/viewing window and an illumination channel/illumination port, although in other embodiments, illumination can be provided by an instrument separate from the biofilm removal endoscope), along with one additional channel that is otherwise permanently affixed relative to the imaging channel(s) through which one of fluid delivery or aspiration is performed.

Although the present disclosure has been described with reference to preferred embodiments, workers skilled in the art will recognize that changes can be made in form and detail without departing from the spirit and scope of the present disclosure.

What is claimed is:

1. A system for removal of bacterial biofilm from a target site of a human patient, the system comprising:
   a biofilm removal endoscope including:
      a handle,
      a controller maintained by the handle,
      an insertion portion adapted for bodily insertion and including a working end, the insertion portion forming:
         an imaging channel terminating at a viewing window formed in the working end that facilitates imaging of the target site, and
         an irrigation channel terminating at a nozzle, the nozzle including a tubular body defining a base end assembled to the working end and an opposite leading end projecting distally beyond the viewing window, the tubular body converging along an axis that extends from the base end to an opening in the leading end that is centrally formed relative to the axis, the nozzle coupled with the controller to rotate the nozzle relative to the working end about the axis,
   wherein the endoscope is configured such that pressurized fluid delivered through the irrigation channel is directed by the nozzle away from the viewing window to impinge upon a layer of bacterial biofilm at the target site.

2. The system of claim 1, wherein the irrigation channel and the imaging channels are permanently affixed relative to one another.

3. The system of claim 1, wherein the insertion portion includes a flexible distal segment.

4. The system of claim 1, wherein at least a segment of the insertion portion is substantially malleable such that the insertion portion is selectively bendable relative to the handle, and further wherein the nozzle is secured to the working end such that the nozzle can be aimed in a desired direction with bending of the insertion portion.

5. The system of claim 1, wherein the insertion portion further forms an aspiration channel terminating at an aspiration inlet formed adjacent the viewing window.

6. The system of claim 5, further comprising:
a source of pressurized fluid fluidly connected to the irrigation channel;
a vacuum source fluidly connected to the aspiration channel.

7. The system. of claim 1, wherein the opening is a V-cut opening.

8. The system of claim 1, wherein the leading end is hemispherical.

9. The system of claim 1, wherein the nozzle is a fan spray-type nozzle that produces a line of mechanical disruption at the target site.

* * * * *